(12) United States Patent
Bieniarz et al.

(10) Patent No.: US 6,303,831 B1
(45) Date of Patent: Oct. 16, 2001

(54) SYNTHETIC METHOD FOR FLUOROMETHYLATION OF HALOGENATED ALCOHOLS

(75) Inventors: Christopher Bieniarz, Highland Park; Kornepati V. Ramakrishna, Libertyville, both of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/587,421

(22) Filed: Jun. 1, 2000

(51) Int. Cl.$^7$ .......................... C07C 43/30; C07C 41/09
(52) U.S. Cl. ..................... 568/604; 568/681; 568/683
(58) Field of Search ..................... 568/604, 683, 568/681

(56) References Cited

U.S. PATENT DOCUMENTS

| | | | |
|---|---|---|---|
| Re. 35,568 | 7/1997 | Halpern et al. | 568/683 |
| 3,549,711 * | 12/1970 | Merrill et al. | 260/614 |
| 3,683,092 | 8/1972 | Regan et al. | 424/342 |
| 4,250,334 | 2/1981 | Coon et al. | 568/683 |
| 4,314,087 | 2/1982 | Radlick | 568/842 |
| 4,469,898 | 9/1984 | Coon et al. | 568/683 |
| 4,847,427 | 7/1989 | Nappa | 568/615 |
| 4,874,901 | 10/1989 | Halpern et al. | 568/683 |
| 4,996,371 | 2/1991 | Halpern et al. | 568/683 |
| 5,705,710 | 1/1998 | Baker et al. | 568/683 |
| 5,789,630 | 8/1998 | Baker et al. | 570/141 |

FOREIGN PATENT DOCUMENTS

| | | | |
|---|---|---|---|
| 727768 * | 4/1955 | (GB) . | |
| 1250928 * | 10/1971 | (GB) . | |
| 97/25303 * | 7/1997 | (WO) . | |

* cited by examiner

*Primary Examiner*—Rosalynd Keys
(74) *Attorney, Agent, or Firm*—Brian R. Woodworth

(57) ABSTRACT

A method for fluoromethylation of a halogenated alcohol. The method includes refluxing a halogenated alcohol with a dihalomethane under basic conditions in a first solvent to form a halomethyl ether and fluorinating the halomethyl ether in the presence of a fluorinating agent.

16 Claims, No Drawings

SYNTHETIC METHOD FOR FLUOROMETHYLATION OF HALOGENATED ALCOHOLS

FIELD OF THE INVENTION

The present invention is directed to a method for fluoromethylation of halogenated alcohols that utilizes transient halomethyl ether intermediates. Treatment of an alcohol with a dihalomethane under basic conditions yields (transiently) a halomethyl ether intermediate which is reacted with a fluorinating agent to form the desired fluoride. The method may be used to synthesize sevoflurane from hexafluoroisopropanol in a single reaction vessel. A method for synthesizing a stable acetal precursor to sevoflurane is also disclosed

BACKGROUND OF THE INVENTION

Anesthetics belong to a class of biochemical depressant drugs which affect the vital functions of cells. Anesthetics generally produce analgesia, loss of consciousness, diminished reflex activity, and muscular relaxation, with minimal depression of the vital functions. Anesthetics may be gaseous (volatile) or fixed (non-volatile). Gaseous anesthetics are inhaled and enter the bloodstream through the lungs while fixed anesthetics are administrated parenterally or through the alimentary canal.

Many currently used gaseous anesthetics are halogenated compounds. These compounds tend to cause less metabolic disturbance and are less flammable than traditional gaseous anesthetic compounds such as ether and cyclopropane. Examples of halogenated anesthetic compounds include halothane ($CF_3CHBrCl$) and trichloroethylene ($Cl_2C=CHCl$) as well as halogenated ether compounds such as enflurane ($CHF_2OCF_2CHClF$), fluroxene ($CF_3CH_2OCH=CH_2$), methoxyflurane ($Cl_2CHCF_2OCH_3$) and isoflurane ($CF_3CHClOCHF_2$).

A particularly useful halogenated ether anesthetic is sevoflurane, $(CF_3)_2CHOCH_2F$, also known as 2-(fluoromethoxy)-1,1,1,3,3,3,-hexafluoropropane or fluoromethyl-1,1,1,3,3,3-hexafluoro-2-propyl ether. Sevoflurane is today one of the most important and widely used general anesthetics. Sevoflurane combines various characteristics that are most desirable in an inhalation anesthetic, including the lowest blood/gas partition coefficient of 0.63, smooth induction and recovery from anesthesia, minimal irritation to the upper respiratory tract, low metabolic rate, and rapid elimination. In addition, sevoflurane is suitable for out-patient surgery use. Although sevoflurane's definitive mechanism of action has not been elucidated, it has recently been shown that sevoflurane interacts with nicotinic acetylcholine receptors by affecting the open and closed state of the ion channels at clinical and lower concentrations. Sevoflurane may also effect reversible modulation of GABA and glycine receptors. The above suggest that at least part of the anesthetic action of sevoflurane may be due to interactions between sevoflurane and specific voltage-gated ion channels.

The preparation of fluorinated compounds such as sevoflurane tends to be difficult because of the limited number of selective fluorination reactions available. Direct fluorination of organic compounds to replace hydrogen is statistical, non-selective, and generally accompanied by the formation of many side products. Hence, fluorinated compounds are usually prepared by first synthesizing a substituted organic intermediate, wherein the substituent group is at the site to be fluorinated, and then displacing the substituent group with a fluoride ion. Metal fluorides, for example, have been used to displace chlorine substituent groups.

Several synthetic routes to sevoflurane employ hexafluoroisopropyl alcohol (HFIP) as a starting material. For example, U.S. Pat. No. 3,683,092 discloses a method for synthesizing sevoflurane involving the methylation of hexafluoroisopropyl alcohol followed by fluorination with either (a) bromine trifluoride, or (b) chlorine gas, followed by potassium fluoride. U.S. Pat. No. 4,469,898 discloses a method for synthesizing sevoflurane which includes the mixing of hexafluoroisopropyl alcohol, formaldehyde, hydrogen fluoride, and a protonating, dehydrating and fluoride ion generating agent. U.S. Pat. No. 4,250,334 discloses a method for synthesizing sevoflurane by adding HFIP to a mixture of a stoichiometric excess of paraformaldehyde and hydrogen fluoride, plus sufficient sulfuric acid to sequester most of the water produced by the reaction. U.S. Pat. No. 4,314,087 discloses a method for synthesizing sevoflurane by reacting HFIP with hydrogen fluoride and a formaldehyde.

The routes disclosed in the referenced patents can result in unwanted by-products which may be difficult to separate from sevoflurane produced by the synthesis. Moreover, the use of corrosive materials in these synthetic routes requires specialized equipment and special handling precautions.

Other methods used to make hexafluoroisopropyl ethers include the conversion of 1,1,1,3,3,3-hexachloroisopropyl ethers to 1,1,1,3,3,3-hexafluoroisopropyl ethers. For example, methyl 1,1,1,3,3,3-hexachloroisopropyl ether and chloromethyl 1,1,1,3,3,3-hexachloroisopropyl ether can be converted to sevoflurane by reaction of each of the above compounds with bromine trifluoride. Hexafluoroisopropyl ethers also can be made by reacting each of these chlorinated compounds with hydrogen fluoride, followed by reaction with bromine trifluoride. U.S. Pat. No. 4,874,901 discloses a method for fluorinating halogenated ether compounds, wherein compounds such as sevoflurane can be prepared by reacting chloromethyl hexafluoroisopropyl ether with either potassium fluoride or sodium fluoride. However, the chlorine replacement methods are not desirable because large volumes of chloride are released in the synthetic process, the yields are low, and multiple chloro-fluoro intermediates are formed. The intermediates must be removed to obtain the final ether product, sevoflurane. The purification processes increase the difficulty and cost of synthesis of 1,1,1,3,3,3-hexafluoroisopropyl ethers by these methods.

Hexafluoropropanes alternatively have been synthesized from malononitrile in the presence of bromine trifluoride, as disclosed in U.S. Pat. Nos. 5,789,630 and 5,705,710.

Another potential route to sevoflurane is by fluorodecarboxylation. Patrick et al., *J. Org Chem.* 48, 4158–4159 (1983), reports that alkyl carboxylic acids can undergo fluorodecarboxylation with xenon difluoride ($XeF_2$) in the presence of hydrogen fluoride. Although the use of xenon difluoride on a small scale can be effective, the cost of xenon difluoride makes its use impractical on a large scale. Furthermore, when alkoxyacetic acids are fluorodecarboxylated with xenon difluoride, significant amounts of side products are formed. Replacement of a carboxylic acid group with a fluorine group has also been disclosed in U.S. Pat. No. 4,996,371 and in RE 35,568 which teach a reaction of hydrogenated aliphatic carboxylic acid compounds with bromine trifluoride; and in U.S. Pat. No. 4,847,427, which teaches a method for preparing fluorocarbon polyethers by neutralizing a perfluorinated carboxylic acid by heating with fluorine in the presence of metal fluoride to replace the carboxylic acid group.

While the above-discussed methods are useful for preparing certain fluorinated compounds, these methods can be complex, expensive, and often provide fluorinated products in low yield together with considerable amounts of side products. Hence there is a need for improved procedures for the preparation of fluorinated compounds.

The present invention provides an improved procedure for preparing fluorinated compounds from the corresponding carboxylic acids in high yield and purity. More specifically, the present invention provides an improved procedure for the preparation of sevoflurane and other similar types of fluorinated anesthetics.

SUMMARY OF THE INVENTION

The invention is directed to a novel method for fluoromethylation of a halogenated alcohol. The method includes the steps of;

(a) combining a halogenated alcohol with a dihalomethane of the formula $CX_2H_2$ (where X is a halogen) under basic conditions in the presence of a first solvent, e.g., polyethylene glycol, to form a transient halomethyl ether; and (b) fluorinating the transient halomethyl ether with a fluorinating agent.

Another aspect of the invention is directed to a method for synthesizing a bis(1,1,1,3,3,3-haloisopropoxy)methane comprising the step of combining a 1,1,1,3,3,3-hexahaloisopropanol and a dihalomethane of the formula $CX_2H_2$ (where X is a halogen) in the presence of a solvent under basic conditions.

Yet another aspect of the invention is a method for synthesizing sevoflurane including the steps of:

(a) reacting 1,1,1,3,3,3-hexafluoroisopropanol with a dihalomethane of the formula $CX_2H_2$ (where X is a halogen) under basic conditions to form a transient halomethylhexafluoroisopropyl ether; and (b) fluorinating the transient halomethylhexafluoroisopropyl ether with a fluorinating agent.

DETAILED DESCRIPTION OF THE INVENTION

As used herein, the term "alkyl" means straight or branched, saturated or unsaturated carbon chains having up to 10, preferably up to 6, and more preferably up to 4 carbon atoms. This term is also meant to encompass alkenyl and alkynyl groups.

The method of the present invention can be performed in a single pot, although it will be appreciated that the described method can be practiced in multiple pots. A "single pot" process is a process that can be performed in a single reaction vessel. It will be appreciated by those of ordinary skill that single pot processes provide certain advantages over multiple pot processes. For example, single pot processes require less handling and/or transfer of components, thereby reducing the risk of accident or mistake. Single pot processes also tend to be less expensive than multiple pot processes as a result of the reduction in handling and transfer of reaction ingredients.

In accordance with one embodiment of the method of the present invention, a halogenated alcohol, e.g., a halogenated alcohol of the formula $R^1C(CX^1_3)_2OH$ (where $R^1$ is selected from the group consisting of hydrogen and alkyl groups and $X^1$ is selected from the group consisting of iodine, bromine, fluorine, and chlorine), is refluxed with a dihalomethane, e.g., a compound of the formula $CH_2X^2_2$ where $X^2$ is selected from the group consisting of iodine, bromine, fluorine, and chlorine, under basic conditions and in the presence of a first solvent to form a transient halomethyl ether of the formula $R^1C(CX_{13})_2CH_2X^2$. It will be appreciated that $X^1$ and $X^2$ can be the same or different in this reaction scheme.

The resulting transient halomethyl ether is fluorinated using a fluorinating agent, thereby producing a fluoromethylated alcohol. It will be appreciated that fluorination can be performed simultaneously with the formation of the transient halomethyl ether, i.e., the method of the present invention produces the desired fluorinated compound in a single-step, single pot process. In the preferred embodiment of the method of the present invention, fluorination of the transient halomethyl ether is performed concurrently with the formation of the transient halomethyl ether.

One example of an appropriate halogenated alcohol useful in accordance with the method of the present invention is hexafluoroisopropanol (HFIP). However, it will be appreciated that other halogenated alcohols can be used without departing from the intended spirit and scope of the invention. For example, secondary halogenated alcohols of the following formula are useful in accordance with the method of the present invention:

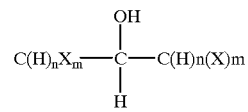

where n is an integer from 0–2 (inclusive), m is an integer from 1–3 (inclusive), and X is fluorine, chlorine, bromine, or iodine. In addition, primary alcohols of the formula $C(H)_nX_mCH_2OH$ (where n is an integer from 0–2 (inclusive), m is an integer from 1–3 (inclusive), and X is fluorine, chlorine, bromine, or iodine) are also useful in accordance with the method of the present invention.

An example of an appropriate dihalomethane useful in accordance with the method of the present invention is dibromomethane. However, it will be appreciated that other dihalomethanes such as $CH_2I_2$, $CH_2F_2$, and $CH_2Cl_2$ can be used without departing from the intended spirit and scope of the invention.

Basic conditions may be attained using known methods such as by the addition of $K_2CO_3$; $Na_2CO_3$; $Cs_2CO_3$; Ba2CO3; or Li2CO3 to the reaction vessel. Persons of ordinary skill in the relevant art will appreciate that there are a large number of alternative methods for attaining basic conditions, including, but not necessarily limited to, the addition of bicarbonates to the reaction vessel.

In one embodiment of the method of the present invention, the reaction is conducted in the presence of a first solvent having the formula $HO-(CH_2CH_2O)_nH$ wherein n is an integer from one to twenty (inclusive), and preferably wherein n is an integer from seven to ten (inclusive). In an exemplary embodiment of the method of the present invention, the first solvent is polyethylene glycol (PEG), preferably PEG 400, i.e., polyethylene glycol having a molecular weight of approximately 400. Other possible first solvents include dimethyl formamide (DMF); n-methyl pyrrolidone (NMP); and dimethyl sulfoxide (DMSO). Persons of ordinary skill in the pertinent art will appreciate that alternative first solvents can be used in accordance with the method of the present invention without departing from the spirit and scope of the present invention.

A co-solvent, e.g., water, can be used without departing from the intended scope of the present invention. For example, a co-solvent may be present in an amount of 0.1% to 5% weight/weight relative to the first solvent.

It will be appreciated that a variety of fluorinating agents can be used in connection with the method of the present invention, including, but not limited to, KF, NaF, KF.HF, and NaF.HF. In a preferred embodiment, KF is used as the fluorinating agent. Those of ordinary skill will understand that various other fluorinating agents can be used in connection with the fluorination step of the method of the present invention.

The disclosed reaction can take place over a wide range of temperatures. For example, the disclosed reaction can be performed efficiently at a temperature from 60° C. to 150° C. In a preferred embodiment, the reaction occurs at a temperature between 90° C. and 100° C. An exemplary temperature is 95° C.

The time required for the reaction may vary widely depending upon many factors, most notably the temperature at which the reaction takes place. For example, reaction times may vary from 1 hour to 20 hours when the reaction is allowed to proceed at a temperature from 60° C. to 150° C. The reaction time is approximately 18 hours at a temperature of approximately 95° C.

After completion of the reaction, the resulting compound can be isolated using a variety of known techniques. For example, the resulting compound can be isolated by adding water to the resulting mixture, partitioning, and then distilling the desired compound from the vessel in which the reaction occurred. This method is particularly useful when the resulting compound is sevoflurane. That is, because sevoflurane is not soluble in water, it will separate into a lower layer in the vessel. In contrast, impurities and solvents present in the resulting mixture are soluble in water, thus allowing the added water and the impurities to be separated easily from the desired sevoflurane.

Another aspect of the invention is directed to a method for synthesizing a bis(1,1,1,3,3,3-haloisopropoxy)methane by refluxing a 1,1,1,3,3,3-hexahaloisopropanol in a first solvent under basic conditions in the presence of a dihalomethane. Appropriate first solvents include, but are not necessarily limited to, PEGs, including PEG400, acetone, and acetone nitrile, as above-discussed. The resulting bis(1,1,1,3,3,3-haloisopropoxy)methane can be converted to sevoflurane using a fluorinating agent such as KF, NaF, KF.HF, and NaF.HF.

In another aspect of the method of the present invention, sevoflurane is synthesized by reacting 1,1,1,3,3,3-hexafluoroisopropanol (HFIP) with a dihalomethane under basic conditions to form a halomethylhexafluoroisopropyl ether by refluxing in a first solvent. Appropriate first solvents include, but are not necessarily limited to, PEGs, including PEG400, acetone, and acetone nitrile, as above-discussed. The halomethylhexafluoro isopropyl ether is fluorinated by refluxing it in the presence of a fluorinating agent. The dihalomethane, fluorinating agent, and reaction conditions used in this aspect of the invention are selected as above-discussed with respect to the first aspect of the method of the present invention.

It is contemplated that other ingredients such as solvents, catalysts, diluents, and other materials may also be present in the reaction mixture if desired, as long as the added extraneous materials do not materially change the nature of the reaction described above, e.g., ingredients added to promote the reaction, suppress side reactions, or improve the purification step of the synthesis.

The following examples are presented for illustrative purposes only, and are not intended to limit the scope of the invention, which is as defined in the claims below. All analyses were conducted by gas chromatography. All percentages are provided in mole percent.

Example 1

Bis(1,1,1,3,3,3-hexafluoroisopropoxy)methane was Synthesized According to Reaction Scheme I as Follows:

To a solution 1,1,1,3,3,3-hexafluoroisopropanol (1.5 mL, 15 mmol) and dibromomethane (1.6 mL, 23 mmol) in acetone ( 5.0 mL) was added $K_2CO_3$(3.15 gm, 23 mmol) and the reaction was heated under reflux. After 18 hours, the reaction mixture was cooled and filtered to remove the solids. The filtrate was distilled to provide bis(1,1,3,3,3-hexafluoroisopropoxy)methane (1.5 g, 52%). This stable acetal precursor to sevoflurane can be deprotectively fluorinated using fluorination procedures known to those skilled in the art.

Reaction Scheme I

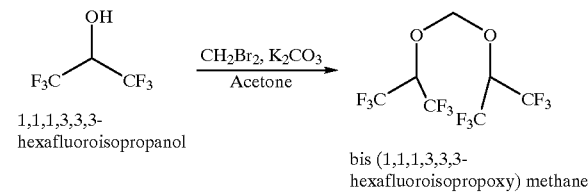

Example 2

Sevoflurane was Synthesized According to Reaction Scheme II as Follows:

To a solution 1,1,1,3,3,3-hexafluoroisopropanol (15 mL, 150 mmol) and dibromomethane (16 mL, 40 mmol) in PEG-400 (60 mL), $K_2CO_3$(31.5 g, 228 mmol) and KF (17.5 g, 300 mmol) were added and the reaction mixture was heated to 100° C. After 18 hours, gas chromatographic (GC) analysis of the reaction mixture indicated 92% conversion of HFIP to sevoflurane. The reaction mixture was diluted with water (100 mL) and the lower organic layer was separated and distilled to provide sevoflurane (12 g, 40%).

Reaction Scheme II

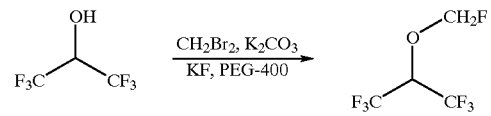

All references herein cited are hereby incorporated by reference.

The present invention is illustrated by way of the foregoing description and examples. The foregoing description is intended to be a non-limiting illustration, since many variations will become apparent to those skilled in the art in view thereof. It is intended that all such variations within the scope and spirit of the appended claims be embraced thereby.

It will be appreciated that changes can be made in the composition, operation and arrangement of the method of the present invention described herein without departing from the intended spirit and scope of the invention as defined in the appended claims.

What is claimed is:

1. A method for fluoromethylating a halogenated alcohol comprising the steps of:

refluxing a halogenated alcohol with a dihalomethane in the presence of a first solvent to form a halomethyl ether; and fluorinating said halomethyl ether using a fluorinating agent.

2. A method in accordance with claim 1, wherein said fluorinating agent and said dihalomethane are added simultaneously to said halogenated alcohol.

3. A method in accordance with claim 1, wherein said fluorinating agent is selected from the group consisting of KF, NaF, KF.HF, and NaF.HF.

4. A method in accordance with claim 2, wherein said first solvent has a formula HO—$(CH_2CH_2O)_n$H wherein n is an integer from one to twenty (inclusive).

5. A method in accordance with claim 4, wherein said first solvent is poly(ethylene glycol).

6. A method in accordance with claim 1, wherein said dihalomethane is dibromomethane.

7. A method in accordance with claim 1, wherein said halogenated alcohol has a formula $R^1C(CX_3)_2OH$, where $R^1$ is selected from the group consisting of hydrogen and alkyl groups, and where X is selected from the group consisting of iodine, bromine, fluorine, and chlorine.

8. A method in accordance with claim 1, wherein said halogenated alcohol has a formula $C(H)_nX_mCH_2OH$, where n is an integer from 0 to 2 (inclusive), where m is an integer from 1 to 3 (inclusive), and where X is selected from the group consisting of iodine, bromine, fluorine, and chlorine.

9. A method in accordance with claim 1, wherein said halogenated alcohol has a formula (I),

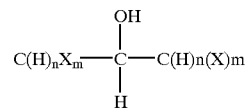

(I)

where n is an integer from 0 to 2, m is an integer from 1 to 3, and where X is selected from the group consisting of iodine, bromine, fluorine, and chlorine.

10. A method for synthesizing a bis(1,1,1,3,3,3-hexahalo-isopropoxy)methane comprising:

refluxing 1,1,1,3,3,3-hexahaloisopropanol in a solvent under basic conditions in the presence of a dihalomethane.

11. A method in accordance with claim 10, wherein said bis(1,1,1,3,3-hexahalo-isopropoxy)methane is bis(1,1,1,3,3,3-hexafluoroisopropoxy)methane.

12. A method for synthesizing sevoflurane, said method comprising:

refluxing 1,1,1,3,3,3-hexafluoroisopropanol with dihalomethane under basic conditions in a first solvent to form a halomethylhexafluoroisopropyl ether; and fluorinating said halomethylhexafluoroisopropyl ether by refluxing said halomethylhexafluoroisopropyl ether in the presence of a fluorinating agent.

13. A method in accordance with claim 12, wherein said fluorinating agent and said dihalomethane are added concurrently to 1,1,1,3,3,3-hexafluoroisopropanol.

14. A method in accordance with claim 12, wherein said fluorinating agent is selected from the group consisting of KF, NaF, KF.HF, and NaF.HF.

15. A method in accordance with claim 14 wherein said first solvent is of the formula HO—$(CH_2CH_2O)_n$H wherein n is an integer from one to twenty (inclusive).

16. A method in accordance with claim 12, wherein said dihalomethane is dibromomethane.

* * * * *